United States Patent [19]

Pekić et al.

[11] 3,983,232

[45] Sept. 28, 1976

[54] NOVEL AGENT FOR TREATMENT OF DEHYDRATIONS IN VETERINARY MEDICINE, PROCESS FOR PREPARATION AND NEW USE THEREOF

[75] Inventors: Branislav Pekić; Vladislav Mladenović; Dragan Cvetković, all of Leskovac, Yugoslavia

[73] Assignee: Zdravlje fabrika farmaceutskih i hemijskih proizvoda, Leskovac, Yugoslavia

[22] Filed: Feb. 18, 1975

[21] Appl. No.: 550,491

[30] Foreign Application Priority Data

Mar. 20, 1974 Yugoslavia............................ 761/74

[52] U.S. Cl.................................. 424/180; 536/112
[51] Int. Cl.².......................................... A61K 31/70

[58] Field of Search.................................... 424/180

[56] References Cited
UNITED STATES PATENTS 2,988,482   6/1961   Novak et al. ........................ 424/180

*Primary Examiner*—Lewis Gotts
*Assistant Examiner*—Cary Owens
*Attorney, Agent, or Firm*—Pollock, Vande Sande & Priddy

[57] ABSTRACT

An agent for the treatment of dehydrations in animals consisting of solutions of dextran or its hydroxy alkyl derivatives; methods for preparing said agent; and the method of treating dehydration in animals by interperitoneally treating affected animals with said agent.

21 Claims, 1 Drawing Figure

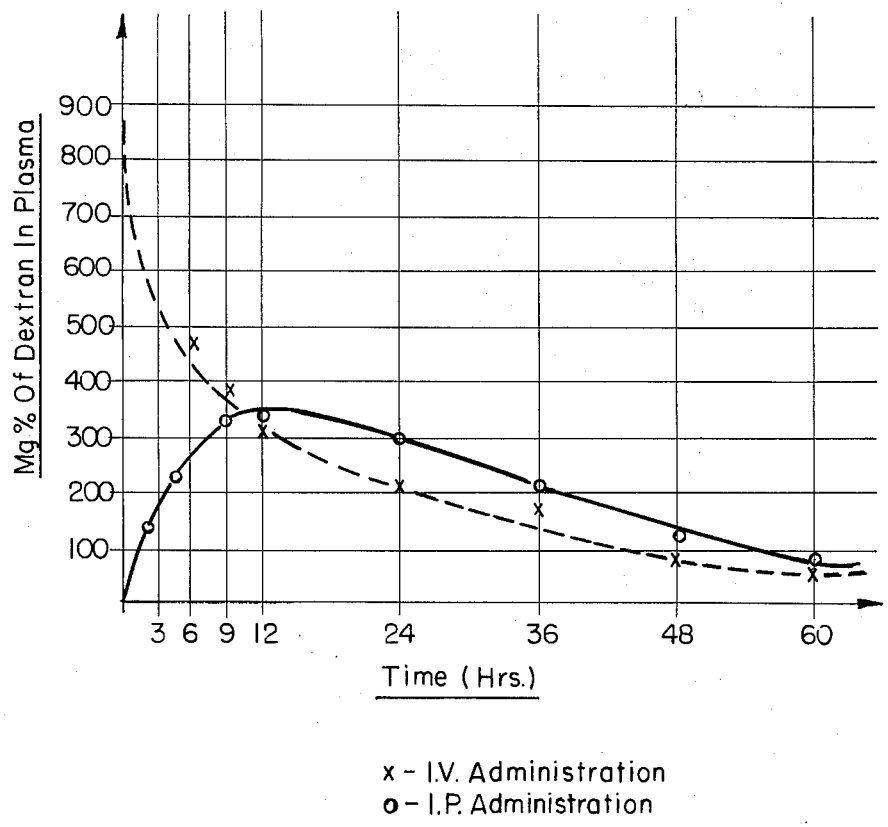

NOVEL AGENT FOR TREATMENT OF DEHYDRATIONS IN VETERINARY MEDICINE, PROCESS FOR PREPARATION AND NEW USE THEREOF

The object of this invention is a new agent which consists of dextran or its hydroxyalkyl derivatives in colloidal solution for prophylaxis and treatment of dehydrations in various etiologies, hypovolemia, hemoconcentration and hypoglycemia, as well as a process for the preparation of this agent and a new use thereof. By the novel agent and the new application thereof, the number of perishments is considerably reduced and the growth of animals is increased.

In the treatment of animal gastro-intestinal diseases followed by diarrhoea, beside antibiotics in practice there are often used various electrolytes for the rehydration and reanimation of the organism. In mass rearing the rehydration of animals by i.v. infusion is difficult to carry out. Peroral administration is not appropriate either because the greater part of the electrolytes is not resorbed but passes through the digestive tract. The remaining electrolytes that reach the circulatory system and the tissue are excreted again, especially in persistent diarrhoea. Hence by such administration lethal anhydremic shock of the affected animals cannot be prevented.

Great losses in the rearing may occur owing to the perishments of animals, especially pigs, as result of starvation, i.e., hypoglycemia, either owing to an overnumber of litter or milk shortage of the sows (agalactia or hypogalactia). For these reasons there has been a continuous need for finding a new effective way of saving the starving animals. Unexpectedly we established that the problem of dehydration of affected animals is solved according to this invention by i.p. application of a solution of dextran or of its hydroxyalkyl derivatives in the physiological solution. We also established that the problem of perishment of animals on the dug owing to starvation and hypoglycemia is completely solved if, according to this invention, the affected animals are treated i.p. by solutions of dextran or its hydroxyalkyl derivatives.

It is known that dextran is used in human medicine as a substitute for lost blood plasma, e.g.:

Lundsgaard-Hansen P: Treatment of Shock with Dextran and Gelatins; Vox Sang., 16, 3, 191–193, 1969

Rosenfield E. L., Saienko A.S.: Metabolism in vivo clinical Dextran, Clin. chim. Acta, 10, 3, 223–228, 1964

Smith M.C.: The Dextrans, Amer. Jour. Hospital Pharm. 22:5, 273–275, 1965

Such a way of dextran application in veterinary medicine is, however, quite different from the application in human medicine, where it is exclusively administered by i.v. infusion to substitute the volume of lost blood or to improve the circulation in the microcirculatory area. In veterinary medicine, according to this invention, dextran or its hydroxyalkyl derivatives are used i.p. as an agent for rehydration of affected animals. For this purpose the i.v. application is out of the question owing to the difficult fixing of the animals, especially when there is a great number of animals to be treated, which regularly occurs in cases of mass diarrhoea.

On the grounds of the use in human medicine, it could not be foreseen that an agent on the basis of dextran or its hydroxyalkyl derivatives could produce so favorable results upon peritoneal injection to dehydrated animals. It should be mentioned that nowadays in human medicine there are used dextrans of weak polydispersity wherein the presence of the molecules of higher weights (over 150,000) is reduced to minimum, whereas for the treatment of dehydration according to this invention, dextrans of greater polydispersity which are more accessible can be used as well.

The use of solutions of dextran or its hydroxyalkyl derivatives according to this invention gives excellent results in the prophylaxis and therapy of hemoconcentrations owing to the loss of water and salt in acute diarrhoea, alimentary poisonings, oedema diseases, enterotoxycosis, coli bacillosis, etc., and in hypoglycemia of young animals.

Further, these favorable results of the therapy of the affected animals by i.p. application of the solution of dextran or its hydroxyalkyl derivatives according to this invention are due to the surprisingly good resorption of dextrans of determined physio-chemical characteristics from the peritoneum. After the i.p. application their concentration in the blood gradually increases and, due to the slow elimination, is kept in the circulatory sytem sufficiently long.

From the attached diagram one can see the change of the dextran concentration in the plasma of pigs after the i.v. and i.p. application of 6 ml/kg of the body weight of 6 % (w/v) dextran solution of an average molecular weight $Mw = 100,000$ in the physiological solution.

In the course of our research we have established that in the treatment of dehydration the highest efficacy is shown by a novel agent which consists of a 1 to 15 % (w/v), preferably 6 to 10 %, dextran solution of an average molecular weight in the range of 30,000 to 300,000, preferably 100,000 to 150,000, in the physiological solution.

It has also been found that the hydroxyalkyl derivatives of dextran (2-hydroxyethyl dextran, 2-hydroxypropyl dextran, 2,3-dihydroxypropyl dextran, 2-hydroxybutyl dextran, 2-hydroxypentyl dextran) of the molecular weights 30,000 to 300,000 of various degrees of substitution, within the range of 0.01 to 0.2, preferably 0.015 to 0.025, are well resorbed from the peritoneum after the i.p. application of their solutions in the physiological solution.

It has also been found that good inventive agents for the prophylaxis and therapy of dehydration are obtained if dextran or its hydroxyalkyl derivatives are dissolved in solutions of crystalloids or mixtures thereof (NaCl, KCl, $CaCl_2$, lactose, glucose), preferably in physiological salt solution.

The i.p. application according to this invention can be administered once or, with more severe cases, it can be repeated. The application of the agent according to this invention can be started on the first day of life, preferably in the period when the symptoms of diarrhoea and dehydration or other etiologies are observed as well as the symptoms of retardation of animals due to starvation.

The quantity of the agent which is administered i.p. is determined depending on the species, age, weight of the animal as well as on the severity of the disease and, most frequently, it varies within the limits of 4 to 10 ml/kg of the body weight.

The following Examples show the resorption of dextran and dextran derivatives from the peritoneum after the circulatory system. They are illustrative of the practical performance of the invention but are not to be construed as limiting.

I. The following tests show good resorption and sufficiently long residence time in the circulatory system of dextran of defined molecular weights after i.p. application.

1. A group of 10 healthy Landras pigs, weighing 6 to 8 kg, 30 to 45 days old, is treated i.p. with 4 ml/kg of the body weight of 6 % (w/v) dextran solution in physiological solution of an average molecular weight, Mw = 70,000. At various time intervals from the moment of application, the contents of dextran is determined in plasma according to the method by J. H. Roe (Jour. Biol. Chem., 208, 889–896, 1954) and the following average values are obtained (Table 1).

Table 1

| Period of time after i.p. application (h) | 6 | 9 | 24 | 36 |
|---|---|---|---|---|
| Contents of dextran in plasma (mg %) | 120 | 285 | 170 | 80 |

2. A group of 10 healthy Landras pigs, weighing 6 to 8 kg, 30 to 45 days old, is treated i.p. with 4 ml/kg of the body weight of 6 % (w/v) dextran solution in the physiological solution of the average molecular weight, Mw = 100,000. At various time intervals from the moment of application, the contents of dextran is determined in plasma according to the above-mentioned method. The following results are obtained (Table 2).

Table 2

| Period of time after i.p. application (h) | 6 | 9 | 24 | 36 |
|---|---|---|---|---|
| Contents of dextran in plasma (mg %) | 170 | 300 | 215 | 170 |

3. A group of 10 healthy Landras pigs, weighing 6 to 8 kg, 30 to 45 days old, is treated i.p. with 4 ml/kg of the body weight of 6 % (w/v) dextran solution in the physiological solution of an average molecular weight Mw = 150,000. At various time intervals from the moment of application, the contents of dextran is determined in plasma according to the above-mentioned method. The following results are obtained (Table 3).

Table 3

| Period of time after i.p. application (h) | 6 | 9 | 24 | 36 |
|---|---|---|---|---|
| Contents of dextran in plasma (mg %) | 170 | 320 | 225 | 215 |

II. The following tests show that the contents of dextran which will be found in the circulatory system depend on the concentration of dextran in the i.p. administered solution, i.e., they prove that by the i.p. application of strictly determined corresponding doses of dextran solutions of various concentrations, by which practically the same quantity of dextran is administered, the same contents of dextran in the circulatory system can be achieved.

4. Groups (A, B, C) each comprising 10 healthy Landras pigs, weighing 6 to 8 kg, 30 to 45 days old, are treated i.p. with 4 ml/kg of the body weight of the solution of dextran of the average molecular weight Mw = 100,000 in physiological solution in various concentrations. Group A is treated with 3 % (w/v) solution, group B with 6 % (w/v) solution and group C with 10 % (w/v) solution. At defined time intervals the contents of dextran in plasma was determined in each animal according to the above mentioned method of J. H. Roe. The results obtained are shown in the following Table (Table 4).

Table 4

| Group | Contents of dextran in plasma (mg %) after i.p. application | | | |
|---|---|---|---|---|
| | 6 h | 9 h | 24 h | 36 h |
| A | 96 | 147 | 81 | 45 |
| B | 170 | 300 | 215 | 170 |
| C | 390 | 506 | 322 | 238 |

III. The following tests prove the good resorption and sufficiently long retention period in the circulatory system of the various hydroxyalkyl dextrans of various degrees of substitution after i.p. application.

5. Groups (A and B), each comprising 10 healthy Landras pigs, weighing 6 to 8 kg, 30 to 45 days old, are treated i.p. with solutions of 2-hydroxyethyl dextrans of various degrees of substitution. Group A is treated i.p. with 4 ml/kg of the body weight of 6 % (w/v) solution of 2-hydroxyethyl dextran of the substitution degree 0.015 and of an average molecular weight Mw = 100,000 in physiological solution. Group B is treated i.p. with 4 ml/kg of the body weight of 6 % (w/v) solution of 2-hydroxyethyl dextran of a substitution degree 0.06 and of an average molecular weight Mw = 100,000 in physiolgical solution. At various time intervals, the contents of 2-hydroxyethyl dextran was determined in plasma, according to the above-mentioned method. The results obtained are shown in the following table (Table 5).

Table 5

| Group | Contents of 2-hydroxyethyl dextran in plasma (mg %) after i.p. application | | | |
|---|---|---|---|---|
| | 6 h | 9 h | 24 h | 36 h |
| A | 120 | 275 | 190 | 150 |
| B | 130 | 250 | 185 | 130 |

6. Groups A and B, each comprising 10 healthy Landras pigs, weighing 6 to 8 kg, 30 to 45 days old, are treated i.p. with 2-hydroxypropyl dextrans of various substitution degrees. The group A is treated i.p. with 4 ml/kg of the body weight of 6 % (w/v) solution of 2-hydroxypropyl dextran of a substitution degree of 0.015 and an average molecular weight Mw = 100,000 in the physiological solution. Group B is treated i.p. with 4 ml/kg of the body weight of 6 % (w/v) solution of 2-hydroxypropyl dextran of the substitution degree of 0.06 and the average molecular weight Mw = 100,000 in the physiological solution. As in the previous Example, the change in the contents of 2-hydroxypropyl dextran in plasma was controlled in dependence of time elapsed from the moment of application of the solution. The results obtained are shown in the following table (Table 6)

Table 6

| Group | Contents of 2-hydroxypropyl dextran in plasma (mg %) after i.p. application | | | |
|---|---|---|---|---|
| | 6 h | 9 h | 24 h | 36 h |
| A | 100 | 295 | 200 | 170 |

Table 6-continued

| Group | Contents of 2-hydroxypropyl dextran in plasma (mg %) after i.p. application | | | |
|---|---|---|---|---|
| | 6 h | 9 h | 24 h | 36 h |
| B | 110 | 270 | 180 | 145 |

IV. The following tests prove the excellent results achieved by i.p. administration of the dextran solution in physiological solution in prophylaxis and therapy of affected animals, which results in an increase of weight and decrease of perishment rate.

7. Group A consisting of 46 starving hypoglycemic Landras pigs without symptoms of other diseases (coli diarrhoea, pneumonia, arthritis etc), 3 to 7 days old, is treated i.p. with 5 ml/kg of the body weight of 6 % (w/v) dextran solution of an average molecular weight $Mw = 100,000$ in physiological solution. The effect of saving starving hypoglycemic pigs in this way was controlled in the course of 10 days related to the control group B. The results obtained are shown in the following table (Table 7).

of the average molecular weight $Mw = 100,000$ in physiological solution in various doses simultaneously with the usual antibiotics therapy. The effect achieved is evaluated on the basis of the degree of dehydration, intensity of diarrhoea, rate of restoring the turgor of the eye cavity and skin elasticity in comparison to the control group of 17 calves which showed disease symptoms of various intensity and which were treated in the same way as the tested group, the only difference being that they received electrolytes orally for the purpose of preventing dehydration instead of the dextran solution. The results of this research are shown in the Tables 8a and 8b referring to the development of the disease of the animals in the investigated and control groups.

The results obtained unambiguously indicate that the way of applying the agents according to this invention has a marked advantage in treating of dehydration caused by diarrhoea as compared to the hitherto applied methods.

9. A group of Simmental calves (17 animals), 3 to 10 days old, with a strong diarrhoea and evident dehydration is treated i.p. with the dextran solution of an aver- Table 7

| Group | Number of pigs | Perishments*) Number | Perishments*) % | Average weight of pigs (kg) At the beginning | Average weight of pigs (kg) After 10 days | Increase of the average weight in % | Activity index in % |
|---|---|---|---|---|---|---|---|
| A | 46 | 2 | 4.4 | 1.683 | 3.049 | 81 | 159 |
| B | 46 | 7 | 15.2 | 1.702 | 2.576 | 51 | 100 |

*)The pigs accidentally killed by sows are not included in the number of perishments.

The results shown demonstrate that by i.p. administration of 6 % (w/v) dextran solution of the average molecular weight $Mw = 100,000$ in physiological solution according to this invention, the perishment rate is decreased by about 3.5 times. It could also be concluded that in the group A which was treated by the dextran solution according to this invention, an increase of weight of 51 % was achieved and the relative increase of the average weight compared to the control group of 59 % was realized.

8. A group of Simmental calves (17 animals) with a moderate diarrhoea without symptoms of dehydration, 3 to 10 days old, is treated i.p. with the dextran solution age molecular weight $Mw = 100,000$ in the physiological solution in various doses, simultaneously with the usual antibiotics therapy. The effects achieved in the therapy are given in Table 9 and are evaluated in comparison to the control group (Table 8a) as in Example 8.

The results obtained evidently emphasize the advantage of this kind of treatment of dehydration of calves in comparison to hitherto applied methods and agents.

TABLE 8a

Effects of the activity of the 6 % (w/v) dextran solution, molecular weight $Mw = 100,000$ in preventing dehydration of calves

| Characteristic No. of the calf | Age (days) | Condition before application DR | Condition before application DH | Duration of the disease (days) | Quantity of the dextran solution (ml) | 1st day DR | 1st day DH | 2nd day DR | 2nd day DH | 3rd day DR | 3rd day DH | 4th day DR | 4th day DH | 5th day DR | 5th day DH |
|---|---|---|---|---|---|---|---|---|---|---|---|---|---|---|---|
| 8854 | 7 | ++ | | 1 | 250 | + | | | | | | | | | |
| 7561 | 8 | ++ | | 1 | 250 | + | | | | | | | | | |
| 7110 | 9 | ++ | | 1 | 250 | | | | | | | | | | |
| 7391 | 5 | + | | 1 | 250 | | | | | | | | | | |
| 8068 | 4 | ++ | + | 2 | 250 | + | | + | | + | | | | | |
| 7684 | 4 | + | | 1 | 250 | | | | | | | | | | |
| 8453 | 5 | ++ | + | 2 | 250 | + | | | | | | | | | |
| 8382 | 4 | + | | 1 | 160 | | | | | | | | | | |
| 3807 | 6 | ++ | + | 2 | 125 | + | | + | | | | | | | |
| 3559 | 5 | ++ | | 1 | 125 | | | | | | | | | | |
| 1423 | 8 | + | | 1 | 125 | | | | | | | | | | |
| 1012 | 9 | + | | 1 | 125 | | | | | | | | | | |
| 3884 | 7 | + | | 1 | 125 | | | | | | | | | | |
| 3835 | 4 | ++ | | 2 | 125 | + | | | | | | | | | |
| 2667 | 3 | ++ | + | 2 | 125 | + | | | | | | | | | |
| 3290 | 3 | ++ | | 1 | 125 | + | | + | | | | | | | |
| 3850 | 5 | + | | 1 | 125 | | | | | | | | | | |

DR - diarrhoea
DH - dehydration

Disease intensity:
+ - poor
++ - moderate

TABLE 8b

Development of the disease in the control group

| Characteristic No. of the calf | Age (days) | 1st day DR | 1st day DH | 2nd day DR | 2nd day DH | 3rd day DR | 3rd day DH | 4th day DR | 4th day DH | 5th day DR | 5th day DH | 6th day DR | 6th day DH | 7th day DR | 7th day DH |
|---|---|---|---|---|---|---|---|---|---|---|---|---|---|---|---|
| 7320 | 2 | + |   | ++ |   | +++ | + | +++ | ++ | ++ | ++ | + | + | + |   |
| 7848 | 3 | + |   | ++ |   | + |   |   |   |   |   |   |   |   |   |
| 8150 | 2 | + |   | + |   | ++ |   | +++ | + | ++ | + | + |   |   |   |
| 8517 | 4 | + |   | + |   | + |   | ++ | + |   |   |   |   |   |   |
| 7495 | 3 | + |   | ++ |   | ++ | + | + | + |   |   |   |   |   |   |
| 7634 | 2 | + |   | ++ |   | +++ | + | +++ | +++ | +++ | +++ | ++ |   | P |   |
| 8054 | 3 | + |   | + |   | + |   |   |   |   |   |   |   |   |   |
| 3916 | 2 | + |   | ++ |   | ++ | + | +++ | +++ | P |   |   |   |   |   |
| 2632 | 4 | + |   | + |   |   |   |   |   |   |   |   |   |   |   |
| 2618 | 2 | + |   | + |   | + |   |   |   |   |   |   |   |   |   |
| 3024 | 4 | + |   | ++ |   | + |   | + |   |   |   |   |   |   |   |
| 3419 | 3 | + |   | ++ |   | ++ | + | ++ | ++ | + | + |   |   |   |   |
| 1116 | 2 | + |   | ++ |   | ++ | + | + |   |   |   |   |   |   |   |
| 1738 | 2 | + |   | ++ |   | +++ | ++ | +++ | + | ++ | + | + |   |   |   |
| 3120 | 2 | + |   | ++ |   | + |   | ++ |   | + |   |   |   |   |   |
| 3316 | 3 | + |   | + |   |   |   | ++ |   | + |   |   |   |   |   |
| 3952 | 5 | + |   | + |   | ++ |   |   |   |   |   |   |   |   |   |

DR - diarrhoea
DH - dehydration
P - perishment

Disease intensity:
+ - poor
++ - moderate
+++ - strong

TABLE 9

Effects of the activity of 6 % (w/v) dextran solution, molecular weight Mw = 100,000, in preventing dehydration of calves with distinct diarrhoea tion of organism, 3 to 10 days old, is treated i.p. with 5 ml/kg of the body weight of 6 % (w/v) dextran solution of the average molecular weight Mw = 100,000 in the physiological solution, simultaneously with the usual treatment with antibiotics. The effect of this treatment of dehydration of suckling pigs caused by diarrhoea is controlled during 10 days relative to the control group B which is treated only with antibiotics. The results

| Characteristic No. of the calf | Age (days) | Condition before the application of the dextran solution DR | DH | Duration of the disease (days) | Quantity of the dextran solution(ml) | 1st day DR | 1st day DH | 2nd day DR | 2nd day DH | 3rd day DR | 3rd day DH | 4th day DR | 4th day DH | 5th day DR | 5th day DH |
|---|---|---|---|---|---|---|---|---|---|---|---|---|---|---|---|
| 9603 | 8 | +++ | ++ | 3 | 250 | ++ | ++ | + | + |   |   |   |   |   |   |
| 02-860 | 7 | +++ | +++ | 5 | 250 | ++ | + | + |   |   |   |   |   |   |   |
| 02-245 | 7 | +++ | +++ | 6 | 250 | ++ | ++ | + | + |   |   |   |   |   |   |
| 9558 | 5 | +++ | ++ | 4 | 500 | + | + |   |   |   |   |   |   |   |   |
| 03-959 | 5 | +++ | ++ | 4 | 500 | + | + |   |   |   |   |   |   |   |   |
| 7985 | 6 | ++ | ++ | 4 | 500 | ++ |   |   |   |   |   | P |   |   |   |
| 8154 | 5 | +++ | ++ | 4 | 500 | + | + |   |   |   |   |   |   |   |   |
| 9315 | 7 | +++ | +++ | 5 | 500 | + | + |   |   |   |   |   |   |   |   |
| 4614 | 6 | +++ | +++ | 4 | 500 | ++ | + |   |   |   |   |   |   |   |   |
| 5843 | 6 | +++ | ++ | 3 | 500 | ++ | + |   |   |   |   |   |   |   |   |
| 07-723 | 4 | +++ | +++ | 3 | 500 | ++ | + |   |   |   |   |   |   |   |   |
| 05-779 | 5 | ++ | ++ | 3 | 500 | + |   |   |   |   |   |   |   |   |   |
| 4721 | 6 | +++ | +++ | 4 | 500 | ++ | + |   |   |   |   |   |   |   |   |
| 4497 | 8 | ++ | ++ | 3 | 500 | ++ |   | + |   |   |   |   |   |   |   |
| 5646 | 10 | ++ | ++ | 3 | 500 | + |   |   |   |   |   |   |   |   |   |
| 07-646 | 10 | ++ | ++ | 3 | 500 | + |   |   |   |   |   |   |   |   |   |
| 07-657 | 10 | ++ | ++ | 3 | 500 | + |   |   |   |   |   |   |   |   |   |

DR - diarrhoea
DH - dehydration
P - perishment

Disease intensity:
+ - poor
++ - moderate
+++ - strong

10. Group A of 35 sucklings Landras pigs with distinct diarrhoea and distinctly affected general condition of organism, 3 to 10 days old, is treated i.p. with 5 ml/kg of the body weight of 6 % (w/v) dextran solution of the average molecular weight Mw = 100,000 in the physiological solution, simultaneously with the usual treatment with antibiotics. The effect of this treatment of dehydration of suckling pigs caused by diarrhoea is controlled during 10 days relative to the control group B which is treated only with antibiotics. The results obtained are shown in Table 10.

Table 10

| Group | Number of pigs | Perishments*) Number | % | Average weight of pigs (kg) At the beginning | After 10 days | Increase of the average weight in % | Activity index in % |
|---|---|---|---|---|---|---|---|
| A | 35 | 1 | 2.85 | 2.185 | 3.456 | 58 | 123 |
| B | 35 | 4 | 11.42 | 2.258 | 3.323 | 47 | 100 |

*)The pigs accidentally killed by sows are not included in the number of perished pigs.

The results shown demonstrate that the i.p. application of 6 % (w/v) dextran solution of an average molecular weight Mw = 100,000 in the physiological solution according to this invention decreases the perishment rate by about 4 times. It can also be concluded that in group A which was treated by the dextran solution according to this invention, an increase in weight of 58 % is achieved, i.e. a relative increase of the average weight of 23 % is realized as compared with the control group B.

11. Group A of 30 early weaned Landras pigs with strong diarrhoea and distinctly affected general condition of the organism, 3 to 10 days old, is treated i.p. with 5 ml/kg of the body weight of 6 % (w/v) dextran solution of an average molecular weight Mw = 100,000 in the physiological solution, simultaneously with the usual antibiotics treatment. The effect of this treatment of dehydration caused by diarrhoea in the early weaned pigs was controlled in the course of 10 days relative to the control group B (30 animals) which was only treated with antibiotics. The results obtained are shown in Table 11.

Table 11

| Group | Number of pigs | Perishments*) Number | % | Average weight of pigs (kg) At the beginning | After 10 days | Increase of the average weight in % | Activity index in % |
|---|---|---|---|---|---|---|---|
| A | 30 | 1 | 3.33 | 5.063 | 6.710 | 33 | 118 |
| B | 30 | 3 | 10.00 | 5.050 | 6.474 | 28 | 100 |

*)The pigs accidentally killed by sows are not included in the number of the perished pigs.

The results shown demonstrate that by i.p. application of 6 % (w/v) dextran solution of the average molecular weight Mw = 100,000 in the physiological solution according to this invention, the perishment rate decreases for about 3 times. It can also be concluded that in group A which was treated by the dextran solution according to the invention, an increase in weight of 33 % is achieved, i.e. the relative increase of the average weight of 18 % is realized in comparison with the control group B.

The agents used in the therapy of the animals as described are prepared by dissolving the active component, i.e., dextran or its hydroxyalkyl derivative in the mentioned suitable solvent in the cited concentration. The solution can be accelerated by heating to a temperature of 90° to 100°C and by stirring.

What we claim is:

1. Method for the treatment of dehydrations in an animal which comprises interperitoneally injecting affected animal with solutions of dextran or of hydroxyalkyl derivative of dextran.

2. The method of claim 1 wherein the dextran or hydroxyalkyl derivative of dextran is dissolved in a solution of a member selected from the group consisting of NaCl, KCl, CaCl$_2$, lactose, glucose or mixtures thereof.

3. The method of claim 2 wherein said solution is a physiological salt solution.

4. The method of claim 1 wherein dextran or hydroxyalkyl derivative of dextran has a molecular weight of 30,000 to 300,000.

5. The method of claim 1 wherein dextran or hydroxyalkyl derivative of dextran has a molecular weight of 100,000 to 150,000.

6. The method of claim 1 wherein the concentration of dextran or hydroxyalkyl derivative of dextran is 1 to 15% (w/v).

7. The method of claim 7 wherein the concentration of dextran or hydroxyalkyl derivative of dextran is 6 to 10% (w/v).

8. The method of claim 1 wherein the hydroxyalkyl derivative of dextran has a substitute degree of from 0.01 to 0.2.

9. The method of claim 1 wherein the hydroxyalkyl derivative of dextran has a substitution degree of from 0.015 to 0.025.

10. The method of claim 1 wherein said hydroxyalkyl derivative of dextran is selected from the group consisting of 2-hydroxyalkyl dextran, 2-hydroxypropyl dextran, 2,3-dihydroxypropyl dextran, 2-hydroxybutyl dextran, 2-hydroxypentyl dextran and mixtures thereof.

11. The method of claim 1 wherein dextran is employed.

12. The method of claim 2 wherein hydroxyalkyl derivative of dextran is employed.

13. The method for the treatment of dehydrations in animals which comprises interperitoneally injecting animals affected with dehydration with dextran or hydroxyalkyl derivative of dextran having a substitution degree of from 0.01 to 0.2 and being selected from the group consisting of 2-hydroxyethyl dextran, 2-hydroxypropyl dextran, 2,3-dihydroxypropyl dextran, 2-hydroxybutyl dextran, 2-hydroxypentyl dextran and mixtures thereof; dissolved in physiological salt solutions of a member selected from the group consisting of NaCl, KCl, CaCl$_2$, lactose, glucose or mixtures thereof.

14. The method of claim 13 wherein dextran or hydroxyalkyl derivative of dextran has a molecular weight of 30,000 to 300,000.

15. The method of claim 13 wherein dextran or hydroxyalkyl derivative of dextran has a molecular weight of 100,000 to 150,000.

16. The method of claim 13 wherein the concentration of dextran or hydroxyalkyl derivative of dextran is 1 to 15% (w/v).

17. The method of claim 13 wherein the concentration of dextran or hydroxyalkyl derivative of dextran is 6 to 10% (w/v).

18. The method of claim 13 wherein the hydroxyalkyl derivative of dextran has a substitution degree of from 0.015 to 0.025.

19. The method of claim 1 wherein said animal is a pig.

20. The method of claim 1 wherein said animal is a calf.

21. The method of claim 1 wherein the amount of said dextran or hydroxyalkyl derivative of dextran is from 4 to 10 ml/kg of body weight of said animal.

* * * * *